(12) United States Patent
DosRamos (10) Patent No.: US 9,046,458 B2
(45) Date of Patent: Jun. 2, 2015

(54) DEVICE FOR USE IN INDUSTRIAL PROCESS ON-LINE DETERMINATION OF PARTICLE SIZE DISTRIBUTION, AND METHODS OF USE

(75) Inventor: J. Gabriel DosRamos, Hopedale, MA (US)

(73) Assignee: Matec Instrument Companies, Inc., Northborough, MA (US)

( * ) Notice: Subject to any disclaimer, the term of this patent is extended or adjusted under 35 U.S.C. 154(b) by 497 days.

(21) Appl. No.: 13/425,603

(22) Filed: Mar. 21, 2012

(65) Prior Publication Data

US 2013/0247656 A1    Sep. 26, 2013

(51) Int. Cl.
| | |
|---|---|
| G01N 15/06 | (2006.01) |
| G01N 15/02 | (2006.01) |
| G01N 29/02 | (2006.01) |
| G01N 15/00 | (2006.01) |

(52) U.S. Cl.
CPC .......... *G01N 15/02* (2013.01); *G01N 2015/003* (2013.01); *G01N 29/02* (2013.01)

(58) Field of Classification Search
USPC ................ 73/1.83, 1.86, 24.01, 24.03, 24.06, 73/61.71, 61.75, 61.79, 64.53, 29 OV, 73/32 A, 54.41, 597, 598, 599, 600, 617
See application file for complete search history.

(56) References Cited

U.S. PATENT DOCUMENTS

| | | | | |
|---|---|---|---|---|
| 5,121,629 | A * | 6/1992 | Alba ............................ | 73/61.41 |
| 6,823,716 | B2 * | 11/2004 | Kelner et al. ................ | 73/24.06 |
| 2002/0121130 | A1 * | 9/2002 | Dosramos et al. ........... | 73/61.75 |
| 2009/0158821 | A1 * | 6/2009 | Sun et al. ..................... | 73/61.75 |
| 2009/0158822 | A1 * | 6/2009 | Sun et al. ..................... | 73/61.75 |

* cited by examiner

*Primary Examiner* — Hezron E Williams
*Assistant Examiner* — Mark A Shabman
(74) *Attorney, Agent, or Firm* — Locke Lord LLP (57) ABSTRACT

A flow-through device for use on-line in a conduit and capable of determining real-time characteristics of particles dispersed in a medium is disclosed. The device uses a sensor and a flow-through cell. The sensor has a stationary transducer positioned in a wall of the flow-through conduit to emit sound waves into the medium and a reflector or a second stationary transducer positioned opposite the transducer. The sensor provides a plurality of different acoustic path lengths through the medium between the transducer and reflector, thereby providing a plurality of different acoustic path lengths in the sensor and no moving parts for the transducer and reflectors. A method for determining the characteristics of particles dispersed in a medium in real time for an industrial process using the flow-through device also is disclosed. Further, a method of controlling particle size distribution in real time in a process using the flow-through device is disclosed.

8 Claims, 5 Drawing Sheets

DEVICE FOR USE IN INDUSTRIAL PROCESS ON-LINE DETERMINATION OF PARTICLE SIZE DISTRIBUTION, AND METHODS OF USE

FIELD OF THE INVENTION

The present invention relates to methods and devices for use in determining the characteristics of particles, including colloids and droplets, dispersed in a medium, particularly to such devices that can be operated on-line in connection with industrial processes and chemical reactors.

BACKGROUND OF THE INVENTION

It often is desirable to know the particle size distribution of particles dispersed in a liquid medium of an industrial process, e.g. a process plant pipe in which the medium is flowing or a chemical reactor. For these reasons, among others, various methods have been used in laboratories on samples from such processes to determine the characteristics of particles in such liquid medium.

One such characteristic is the particle size distribution (PSD). See, for example, U.S. Pat. Nos. 4,706,509, 5,121,629, and 5,569,844. U.S. Pat. No. 4,706,509 describes a method for ultrasonically measuring solids concentration and particle size distribution in a dispersion. Ultrasonic waves at a variety of frequencies are directed into the dispersion, and the attenuation at these frequencies is measured. A dimensional spectrum (across the range of particle dimensions) is divided into dimensional intervals, and a system of linear equations is developed to represent the concentration of particles in each dimension interval. The system of equations is then solved to determine the PSD.

The process described in U.S. Pat. No. 5,569,844 involves measuring the attenuation of both ultrasonic waves and electromagnetic radiation to determine particle size distribution. Specifically, ultrasonic velocity and ultrasonic attenuation are combined with the density, as determined from the electromagnetic radiation attenuation, to calculate the PSD. In addition to the problems inherent in generating x-rays or gamma rays, however, particle sizes of about 10 to 15 μm appear to be the lower limit for the process.

In U.S. Pat. No. 5,121,629, ultrasonic waves at a variety of selected frequencies are passed through a dispersion, and the attenuation at each frequency is measured to derive a measured attenuation spectrum over those frequencies. Separately, based on a theoretical model, a set of attenuation spectra are calculated for a variety of PSDs, and the calculated spectra are then compared to the measured spectrum to formulate a preliminary approximation of the PSD of the dispersion. Further calculations must be performed, starting from this approximation, to more accurately determine the PSD.

U.S. Pat. No. 6,119,510 describes an improved process for determining the characteristics of dispersed particles. The term particles is used to include solids, liquids, or gases dispersed in a continuous medium. Waves (acoustic or light) are directed into a dispersion, and the attenuation of the waves for particular frequencies is measured to provide an attenuation spectrum. The measured attenuation spectrum is then compared to a set of theory-based calculated attenuation spectra to determine the particle size distribution corresponding to the measured attenuation spectrum. Unlike previous processes, the particle size distribution is capable of being accurately determined by a single inversion algorithm. Inversion techniques involve taking a set of known particle size distributions, determining the attenuation spectrum that each PSD would theoretically produce, and comparing a set of such theory-based spectra to the actual, measured spectrum to find the actual PSD.

Acoustic attenuation techniques for characterizing particles in dispersions involve the interaction of applied sound waves with the dispersed particles. As a sound wave travels through a dispersion, the wave loses acoustic energy by various scattering mechanisms. Measurement of the attenuation at different frequencies of the sound wave leads to an acoustic attenuation spectrum. Models by Epstein and Carhart (Acoust. Soc. Am. 25, 553 (1953)), and by Allegra and Hawley (Acoust. Soc. Am. 51, 1545 (1972)) make it possible to predict the attenuation spectrum for particles of a given size distribution and concentration. The models require knowledge of several physical properties of the particles and the liquid medium, including density, thermal expansion coefficient, thermal conductivity, heat capacity, viscosity, and shear rigidity. It is then possible to construct a 3-D matrix that relates attenuation, frequency, and particle size.

Acoustic attenuation in a particle dispersion can be measured by use of an apparatus such as the Ultrasizer™, made by Malvern Instruments, Ltd., Worcestershire, United Kingdom (the assignee of U.S. Pat. No. 5,121,629, discussed above). A schematic of the chamber 110 of such an apparatus is illustrated in FIG. 7 of U.S. Pat. No. 6,604,408. There, two pairs of broadband transducers 112, 114, 116, 118, are in contact with a sample located in a tank 120, typically formed of stainless steel. Typically, one pair of transducers 112, 114 covers a lower frequency range, e.g., 1 to 20 MHz, and the other pair 116, 118 a higher range, e.g., 15 to 200 MHz. Generally, the transmitting transducers 112, 116 are capable of being moved to different positions in the chamber, but the receiving transducers 114, 118 are fixed. The spacing between the transmitting transducers 112, 116 and the receiving transducers 114, 118 is controlled by a stepper motor.

U.S. Pat. No. 5,121,629, discloses a through-transmission device useful for industrial on-line measurement and control of slurries that uses at least one pair of acoustic transducers wherein one of the pair is moved by a stepper motor in order to perform attenuation measurements at various acoustic path lengths.

Problems with the prior art devices, such as apparatus described above, include wear of the seal due to the translation movement of the receiving transducers. That wear causes misalignment of the receiving transducer with the emitting transducer causing major degradation of results due to minute levels of misalignment. The transducers move up to about four inches and, thus, considerable wobble can be experienced due to movement on the o-ring seal. The wear of the seals also can result in leaking of the sample, which can result in a change of the volume sample, i.e., the level of the sample in the sample cell changes. Further, the in/out movement of the variable position transducers in the sample cell and resultant leakage can cause significant changes in the sample level in the cell. The change in the volume/level of the sample can result in the introduction of sound waves reflected from the liquid surface or a change in the reflection pattern, thereby further degrading the results. Besides sample loss, leaks also can cause electrical damage to the device and sample change. For example, the percent of solids in the sample can increase if the medium is leaked. Also, the shear applied on samples by friction between a moving transducer and an o-ring can cause the particles to aggregate (to form clusters). This particle aggregation can shift the measured particle size to a larger value, thereby rendering the data inaccurate.

Constant wear and tear of the o-ring seal and transducer causes progressive loss of alignment that leads to progressive degradation of data. Thus, frequent replacement of the o-ring seals is required along with tedious alignment of the transducers after each replacement.

In order to produce true, accurate, high-resolution, broad-particle-size range PSD data, Acoustic Attenuation Spectroscopy measurements are made over a wide acoustic frequency range of at least 4-20 MHz and preferably 4-80 MHz or higher. Particles attenuate sound more efficiently at acoustic wavelengths close to their particle size, i.e., larger particles attenuate sound more efficiently at low frequencies while smaller particles do so at higher frequencies of the sound wave.

In order to achieve such broadband (true) spectra, attenuation measurements typically are made at a minimum of two acoustic path lengths. Using multiple path lengths enables measurements over broader frequency ranges due to the fact that attenuation increases monotonically with frequency, i.e., optimal signal-to-noise measurements can be performed as follows: higher-frequency data (where attenuation is higher) can be collected at shorter paths while low-frequency attenuation data can be measured at longer paths.

Measurements at multiple path lengths also enable the determination of the acoustic fixed loss at the various sensor interfaces such as within the ultrasonic transducer delay rod, and at this rod's liquid interface, and acoustic reflectors, if present (see Reed, R. W., DosRamos, J. G., and Oja, T., *Review Quant. Nondestr. Eval,* 21, Thompson, D. O. and Chimenti, D. E., Ed., pp. 1494-1501 (2001)).

U.S. Pat. No. 6,604,408, discloses a device that uses an acoustic reflector introduced through the top of a sample cell. The reflector is moved within the sample cell to position it at various path lengths to measure the returning acoustic echoes from two transducers. This device eliminates the need to move acoustic transducers through walls of the sample cell.

The use of moving parts is undesirable for continuous process on-line operation, and the relatively long time required for the acquisition of the attenuation-spectrum data due to the need to re-position the transducers or reflectors hinders or prevents real-time data generation.

Although current apparatus for characterizing dispersed particles, e.g., determining PSD, are adequate, improvements to devices that can determine PSD on-line, and particularly in real time, in industrial processes are desired.

SUMMARY OF THE INVENTION

The present invention provides a new device capable of real time determination of the particle size distribution (PSD) of particles dispersed in a medium of an industrial process. The device comprises a conduit open at both ends and connected to the industrial process for analyzing particles dispersed in the medium from the process. The conduit may be part of the process piping or a by-pass conduit attached to process piping or other process elements. The medium can flow through one end of the device and out the opposite end, preferably back into the process. The device comprises a sensor that provides a plurality of different acoustic path lengths through the medium without moving parts. The sensor comprises a stationary transducer positioned to emit sound waves into the medium through a wall of the device. Opposite the transducer is(are) (i) a fixed reflector(s) or mirror surface(s) or (ii) a second stationary transducer. The transducer(s) and reflector(s) are structured and arranged to provide a plurality (i.e., two or more) fixed acoustic path lengths between (a) a stationary transducer and the opposing fixed reflector surface or (b) between a pair of opposing stationary transducers. Acoustic particle analysis devices in accord with this invention provide for broadband acoustic attenuation spectroscopy measurements of particles, including concentrated colloids and droplets, over a range of ultrasonic frequencies using a flow-through sample cell. The sample cell can be positioned, for example, in a process plant pipe, or by a storage vessel or a chemical reactor, or the like. The cell in accord with this invention is suitable for industrial process on-line measurements due to its lack of moving parts along with minimized abrasion effects from the flowing particles or colloids, and the like.

In one embodiment, the fixed acoustic path lengths are provided by a plurality (i.e., two or more) of stationary mirror surfaces, each surface positioned at a different fixed length from the transducer and positioned to reflect sound waves emitted by the transducer. The plurality of stationary mirror surfaces may be provided, for example, by a plurality of separate mirror surfaces or by a single mirror device having a plurality of stepped mirror surfaces. Thus, in one instance, a device in accord with the present invention comprises a conduit wherein the wall of the conduit opposite the fixed transducer has a plurality of stepped mirror surfaces, each surface positioned at a different length from the transducer and positioned to reflect sound waves emitted by the transducer. Preferably, the surfaces are stepped such that, in the direction of fluid flow, the first surface in the direction of the fluid flow is closest to the transducer and each succeeding mirror surface is more distant from the transducer. In another instance, the plurality of mirror surfaces are fixed within the conduit at different fixed lengths from the transducer and positioned to reflect sound waves emitted by the transducer.

In another embodiment of the invention, the fixed acoustic path lengths are provided by configuring a buffer delay rod for the transducer to have a stepped surface facing a single reflector, the buffer delay rod having a plurality (two or more) steps providing different fixed distances between the end of the rod and the reflector.

In a further embodiment of the invention, two fixed transducers are positioned opposite a plurality of stationary mirror surfaces, each surface positioned at a different fixed length from the transducers and positioned to reflect sound waves emitted by the transducers.

In the above acoustic reflection embodiments, preferably the transducer is used both as the emitter and the receiver.

The present invention can also be implemented for through-transmission acoustic attenuation. In through transmission embodiments, in accord with the present invention, a pair of stationary transducers are positioned in opposing orientation on walls of the flow-through conduit. At least one of the transducers is configured with a buffer delay rod having a plurality (two or more) steps providing different fixed distances between the end of the rod facing the opposing transducer.

Devices of the invention can make measurements at multiple acoustic path lengths but without having to move any acoustic sensors or reflectors. This arrangement eliminates the need for expensive, and maintenance prone motion stages or stepper motors.

Additionally, the stepped reflector, as well as, the emitter/receiver transducer or the pair of opposing transducers are positioned so that abrasion from the flowing particles is minimized.

The sensors in devices of the present invention preferably are located in a by-pass conduit to facilitate, for example, maintenance and cleaning of the device and to reduce wear by controlling the flow rate through the sensor.

The sensor in devices of the present invention can be used to measure properties of sound waves including attenuation of sound waves by the medium and the sound speed of sound waves for particular frequencies to provide an attenuation spectrum or a sound speed spectrum, respectively.

Using devices in accord with various embodiments of this invention, multiple-frequency measurements can be made quickly—without pausing to move transducers or reflectors—in order to ensure that the data is collected in real time on a representative sample.

Devices in accord with this invention also can reduce or eliminate the need to move acoustic transducers or reflector shafts through o-rings positioned on the cell wall. Such o-rings, transducers, and reflector shafts can be subject to intense abrasion from friction from the flowing particles.

Acoustic attenuation spectroscopy measurements allow the determination of PSD of concentrated particles in various products such as, for example, paints, inks, ceramic slips, oil/water and water oil emulsions, semiconductor polishing slurries, etc. Unlike laser-based instruments, acoustic measurements offer the advantage that measurements can be made on samples at process conditions, without sample dilution.

Devices in accord with the present invention allow broadband acoustic attenuation spectroscopy measurements of concentrated particles over a range of ultrasonic frequencies using a flow-through sample cell. This sample cell can be positioned for on-line analysis of industrial media by locating it, for example, on a process plant pipe, a chemical reactor or storage tank. Preferred embodiments of the on-line cell of the present invention do not use moving parts which facilitates reliable continuous operation 24/7, minimize abrasion effects from the flowing particles, and enable real-time data acquisition through rapid simultaneous multi-path attenuation measurements.

Devices in accord with this invention can enable implementation of process control systems at particle production plants such as those mentioned above. Examples use of devices of the present invention for process control instances are as follows:

Printers utilized for creating decorative patterns on ceramic tiles. These printers use inks whose particle size distribution features are fundamentally important in obtaining the desired resolution and general quality of these prints. These printers are used at most—if not all—plants for high-quality ceramic title production.

Semiconductor Chemical Mechanical Polishing (CMP) machines utilized in the production of advanced semiconductor chips nowadays. These CMP tools would benefit from monitoring the PSD of the incoming abrasive slurries used in this polishing process.

Other examples of industries interested in particle size distribution on-line monitoring are as follows: paints, ceramic slips, pharmaceuticals, cosmetics, foods (including milk), minerals extraction and processing, crude oil extraction, etc.

The present invention also provides a method for determining the characteristics of particles dispersed in a medium in real time for an industrial process. The method comprises providing a flow-through device for use on-line in a by-pass conduit for determining real-time characteristics of particles dispersed in a process medium, the device comprising a sensor in a flow-through conduit. The sensor can comprise an acoustic reflection particle analysis device or a through-transmission acoustic particle analysis device, such as described above, having a plurality of different acoustic path lengths. A sample from a process is permitted to flow into the sensor from the by-pass conduit for the sensor to determine the characteristics of the particles. Attenuation of sound waves for various particular frequencies are obtained to provide an attenuation spectrum. Measurements at multiple path lengths allows the calculation of the slope of attenuation (dB) versus path length (cm) at each frequency for accurate attenuation spectra in dB/cm vs. frequency, as well as, sound speed spectra. Also, sound speed of sound waves for the particular frequencies can be obtained to provide a sound speed spectrum.

The invention also provides a method of controlling particle size distribution in real time in a process. A flow-through device in accord with the invention can determine real-time characteristics of particles dispersed in a process medium. The attenuation spectrum or sound speed spectrum can be used to control a process parameter to maintain desired characteristics of the particles in the process medium.

As used herein, the term "particle" is a generic term that includes, for example, colloids and emulsion droplets such as oil-in-water, as well as, water-in-oil emulsions.

DETAILED DESCRIPTION OF THE INVENTION

Including Preferred Embodiments Thereof

The present invention provides a device used for on-line determining the characteristics of particles dispersed in a medium. A process for determining the characteristics of the particles involves directing acoustic waves into a dispersion of the particles and measuring the attenuation of the sound waves for particular frequencies to provide an attenuation spectrum. An inversion technique is performed to determine the particle size distribution corresponding to the measured attenuation spectrum. The measured attenuation spectrum is compared to a set of theory-based calculated attenuation spectra. A preliminary approximation of the particle size distribution is not required. See, for example, U.S. Pat. No. 6,119,510, the disclosure of which is hereby incorporated by reference.

Figure 1:
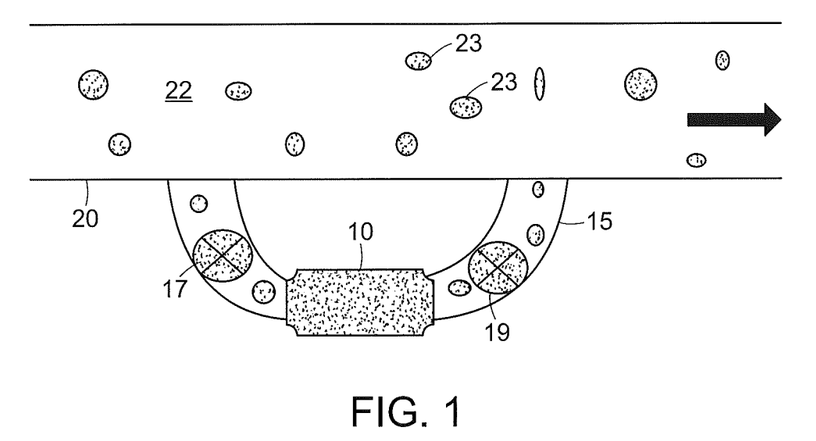
FIG. 1 is a schematic illustrating on-line implementation of a flow-through sensor on a pipe in accord with one embodiment of the present invention.

With reference to the drawings, the implementation of a flow-through device, i.e., an acoustic reflection particle analysis sensor (AREPA) in accord with one embodiment of the present invention is illustrated. As illustrated in FIG. 1, the device 10 is positioned in by-pass conduit 15, which is connected to a pipe 20 carrying a fluid 22 containing particles 23 in an industrial process, the arrow showing the direction of flow. This sensor can also be installed in vertical or other positions. Valves 17, 19 permit flow through the device for making particle size analyses when desired. Suitable valves also preferably allow for flow of calibration and/or cleaning fluids, as desired.

Figure 2:
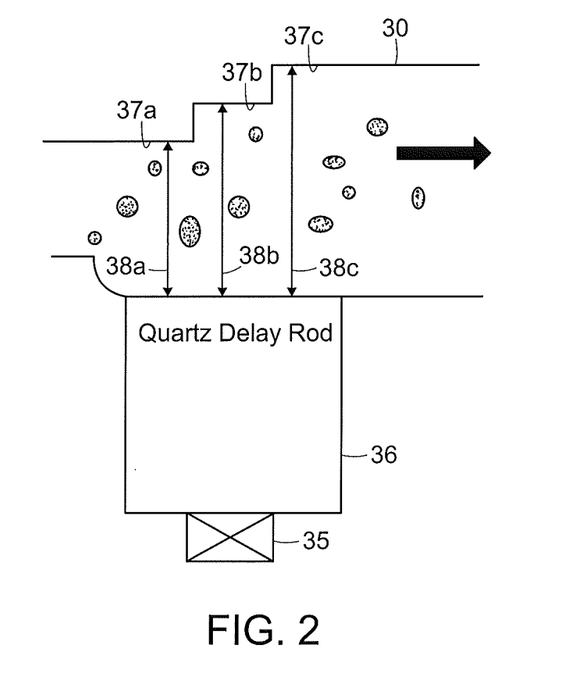
FIG. 2 is a schematic illustrating an arrangement whereby three continuous steps on a fixed acoustic reflector/mirror provide three different acoustic path lengths for nearly simultaneous attenuation measurements at various frequencies in accord with one embodiment of the present invention.

As illustrated in FIG. 2, a sensor in accord with one embodiment of the invention comprises the device 10 in FIG. 1. The sensor has an internal configuration as illustrated in FIG. 2. A conduit 30 inside the device receives flow of the medium from the by-pass conduit, in which the device is positioned. On one side of the conduit 30 is positioned a transducer assembly that includes a transducer 35 and a quartz delay rod 36. Opposite the transducer assembly is a stepped mirrored surface having three sections with mirrored surfaces 37a, 37b, 37c thus providing three different length echo paths 38a, 38b, 38c for the emissions from the transducer 35.

Figure 3:
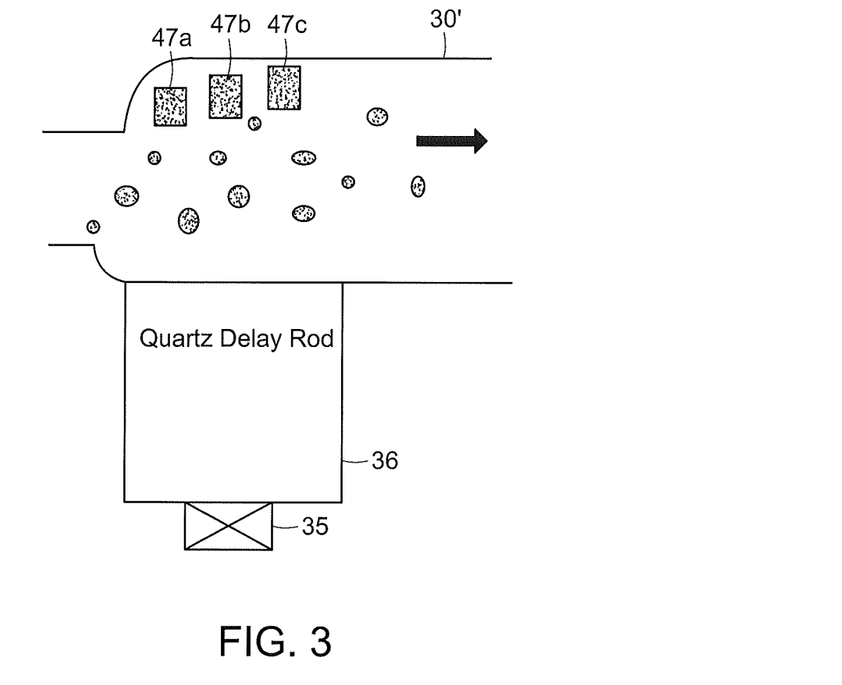
FIG. 3 is a schematic illustrating another embodiment in accord with the present invention wherein three different path lengths are provided by three separate stationary reflectors.

FIG. 3 illustrates another embodiment for a sensor in accord with the invention where like reference numbers are used for elements that are the same as those in FIG. 2. In this embodiment the stepped mirrored surfaces in FIG. 2 are replaced with separate mirrored surfaces 47a, 47b, 47c to provide three different length echo paths for the emissions from the transducer 35. Conduit 30' has a curved surface adjacent the separate mirrored surfaces for better flow in that vicinity. Additional stepped surfaces on the end of the buffer delay rod can be added as desired.

Figure 4:
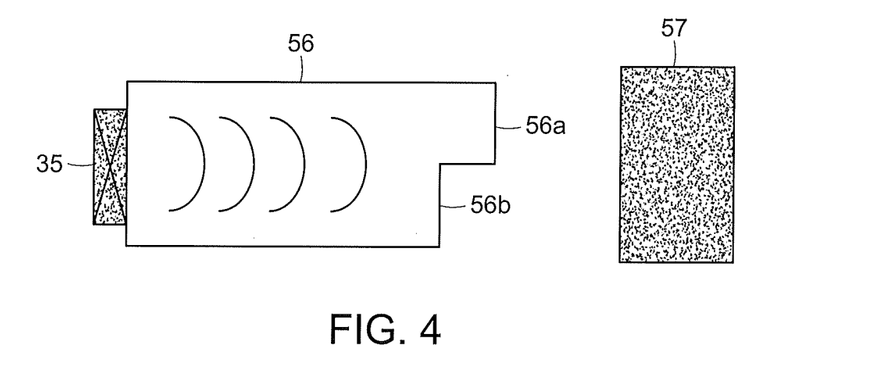
FIG. 4 is a schematic of an ultrasonic transducer with a buffer delay rod configured so that attenuation can be measured at two fluid echo paths with a single reflector surface.
Figure 5:
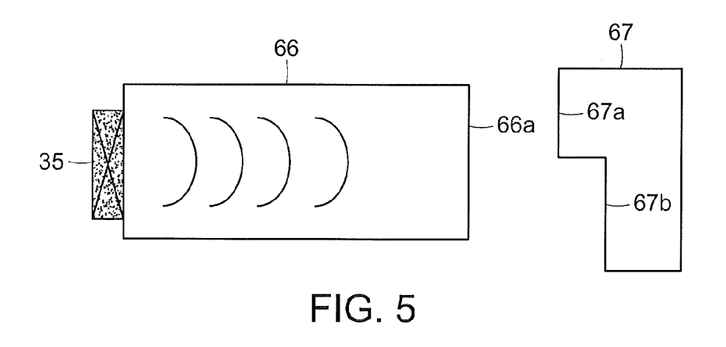
FIG. 5 is a schematic of a transducer assembly with a stepped mirrored surface that can be configured equivalent to the combination in FIG. 4 so that attenuation can be measured at two fluid echo paths with a single reflector device having two stepped mirror surfaces.

Other alternative configurations for the sensor are illustrated in FIGS. 4 and 5. In FIG. 4, the transducer assembly includes a transducer 35 and a buffer delay rod 56 that has stepped surfaces 56a, 56b facing the mirrored surface 57. The stepped surfaces of the buffer delay rod provide two different length echo paths for the emissions from the transducer 35 using only one mirrored surface 57. The configuration illustrated in FIG. 5 is similar to that illustrated in FIG. 2 and provides two different length echo paths for the emissions from the transducer 35. However, in this embodiment, the buffer delay rod has a single surface 66a and the reflector 67 has two mirrored surfaces 67a, 67b. Additional stepped mirrored surfaces can be added as desired.

In the sensor, an opening (not shown) is provided in side wall of the sensor to sealingly hold the transducer assembly. One transducer 35 is illustrated. However, a second transducer can be positioned in an arrangement to emit and receive echoes from the same reflector surface. For example, one of the transducers emits sound waves having a frequency in the range of from about 1 to about 25 MHz. The second transducer emits sound waves having a higher frequency in the range of from about 10 to about 100 MHz. This enables faster analysis of particle characteristics, if desired. The opposite end of the transducer is held typically by an alignment ring (not shown) that is used to align the transducers for optimal performance, as is well known to those skilled in the art. Thus, one end is mounted sealingly in the opening in the side wall and the other end is supported in the alignment ring. The structure is supported as necessary to maintain stability, as is well known in the art. Typically, three extremely fine alignment screws (e.g., 80 pitch thread; not shown) spaced 120 degrees apart are provided.

A transducer output signal pre-amplifier preferably also is provided (not shown) for the sensor.

Figure 6A:
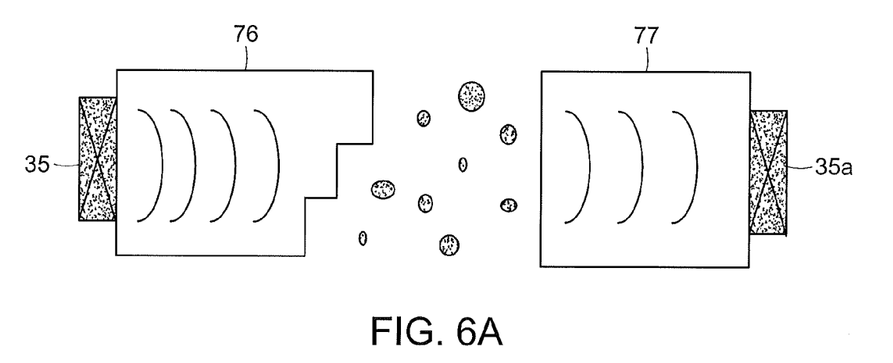
FIG. 6(a) is a schematic illustrating a through-transmission embodiment in accord with the present invention wherein a pair of opposing ultrasonic transducers are used with one of the transducers having a buffer delay rod configured to provide three different acoustic path lengths.
Figure 6B:
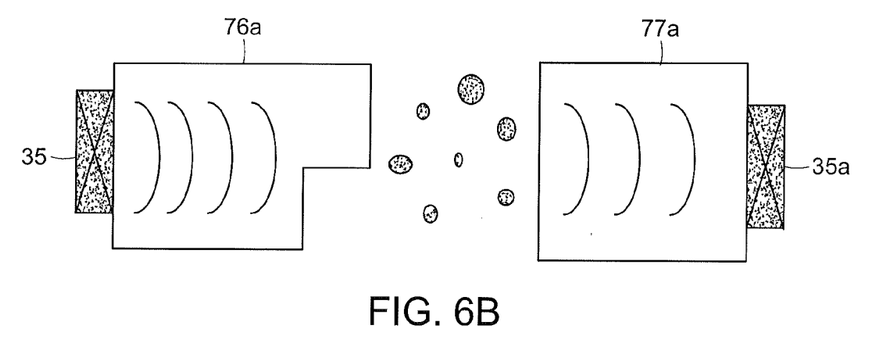
FIG. 6(b) is a schematic similar to FIG. 6(a), but one transducer having a buffer delay rod configured to provide two different acoustic path lengths.

The concepts of the present invention also can be implemented in a through-transmission acoustic particle analysis device. In a through-transmission device, a pair of ultrasonic transducers are positioned opposing each other with the fluid space between. Careful alignment of the transducers is important, as is well known to those skilled in the art. At least one of the transducers must be assembled with a buffer delay rod having a stepped surface facing the opposing transducer so as to provide a plurality of different length acoustic paths. Examples of suitable configurations are provided in FIGS. 6(a) and 6(b). In those examples, both of the opposing transducers 35, 35a are assembled with a buffer delay rod 76, 77 and 76a, 77a. More than one pair of such opposing transducers can be used to provide the desired acoustic frequency range, typically 1-100 MHz.

Figure 7:
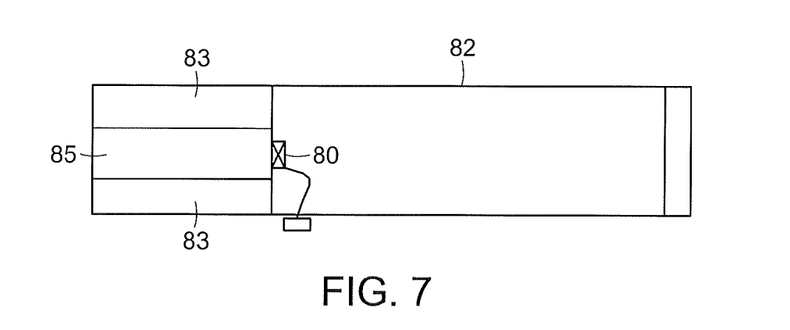
FIG. 7 is a schematic side view of an example of a transducer assembly for use in the present invention.
Figure 8:
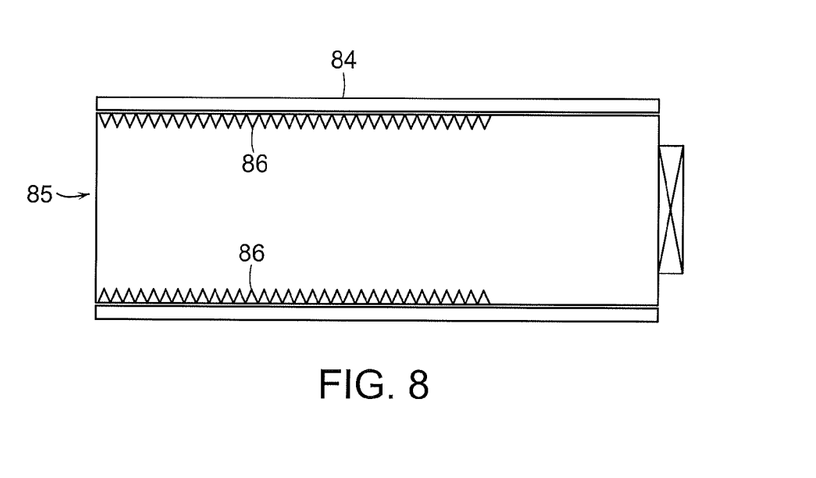
FIG. 8 is a schematic side view of an example of a quartz delay rod for use in a transducer assembly of the present invention.

A typical transducer assembly useful in the present invention is illustrated in FIG. 7, wherein a transducer 80 is housed in a continuous tube 82 having sufficient length to house the transducer and accommodate desired alignment accuracy. For example, a length of about 15 inches is satisfactory for the tube for certain embodiments. A quartz buffer rod 85 preferably is positioned between the transducer and the sample to delay the sound waves. The delay facilitates using the transducer for both an emitter and a receiver. A 19.5 µsec delay has been found satisfactory for certain embodiments. The quartz rod preferably has grooves 86 to reduce undesirable sound echoes (noise) (see FIG. 8). These echoes can overlap with and, thus, distort the desirable attenuated sound waves. Grooves having a depth of 0.035 inch are suitable. The quartz rod 85 is held by epoxy 84 in a resin sleeve 83 inside the tube 82. A Delrin® material is suitable for the resin sleeve 83. A tungsten-loaded epoxy is suitable for dampening the undesirable sound echoes. The tube 82 preferably is a stainless steel tube. Other suitable materials are readily substituted by those skilled in the art.

A difference between using one flat receptor and a multi-step reflector or differently spaced receptors is, for example, that the reflection from the middle of three reflector surfaces is larger than from the side ones, because the middle reflector surface reflects more of the core of the waveform. However, this difference does not present a problem because corrections can be made by performing a regular calibration, e.g., with water or the fluid being monitored. Such calibration is also used with the regular lab device (having a flat single reflector).

Because using a device in accord with the present invention divides the waveform into as many parts as there are reflectors of different steps in the wave path, the resulting echoes or transmissions are smaller by the same ratio relative to a single reflector or equivalent transmission surface. Thus, when implementing on-line devices in accord with the present invention, the size of the transducer and delay rod preferably are adjusted accordingly in connection with the multi-step surfaces. For example, to minimize this ratio effect, it may be preferred to use a 2-inch diameter delay rod as opposed to the current 1-inch illustrated above, and also to use a larger 1.5" transducer element instead of the ¾" element. That will put more energy into the sample and get larger echoes back from the reflectors. A similar result can be expected when using transmission multi-step sensors.

In addition, it may be preferred to make the online Quartz delay rod about 50% longer for devices of the present invention in order to accommodate more easily the multiple echoes generated by the multiple reflectors or stepped transmission surfaces.

The specific dimensions for components can be optimized for particular applications by routine experiments using procedures well-known to those skilled in the art.

The structural elements of the device 10 can be made from any suitable material. Preferably, the material is selected based on the fluid used in the industrial process being monitored by the sensor to reduce or avoid chemical attack and wear due to the particles. Suitable materials are readily selected by those skilled in the art.

With a device in accord with the present invention, there are no seals required for a moving transducer. Thus, there is no degradation of performance do to seal wear and misalignment caused thereby. There is no wear on the seals or the transducers in a device according to the present invention. Also, the liquid level remains constant and sound is not reflected off the liquid surface in a varying manner during sample testing. This liquid surface reflected sound can overlap with, and thereby distort, the desired attenuated sound wave. The present invention eliminates the need to replace seals for a moving transducer and the necessary alignment of transducers after such replacement. Devices in accord with the present invention are capable of providing more consistent long term accuracy and reproducibility of results with lower maintenance than prior art devices.

Very fine alignment is required whether an emitter/receiver transducer pair or an emitter/reflector pair setup is used. In fact, the prior art emitter/receiver setup requires that both transducers be aligned relative to each other thereby making the alignment process more tedious and time consuming. In the proposed invention, only the transducer need be aligned against a perpendicular reflector surface.

Attenuation is preferably measured at multiple spacings for three reasons as follows: (i) high frequency measurements must be made at narrow paths while the opposite happens at low frequencies; (ii) the attenuation curve must be built with as many as 100 data points in order to produce reliable particle size distribution data; and (iii) slopes of attenuation versus distance can be precisely measured for accurate attenuation, as well as, sound speed spectra.

Figure 9:
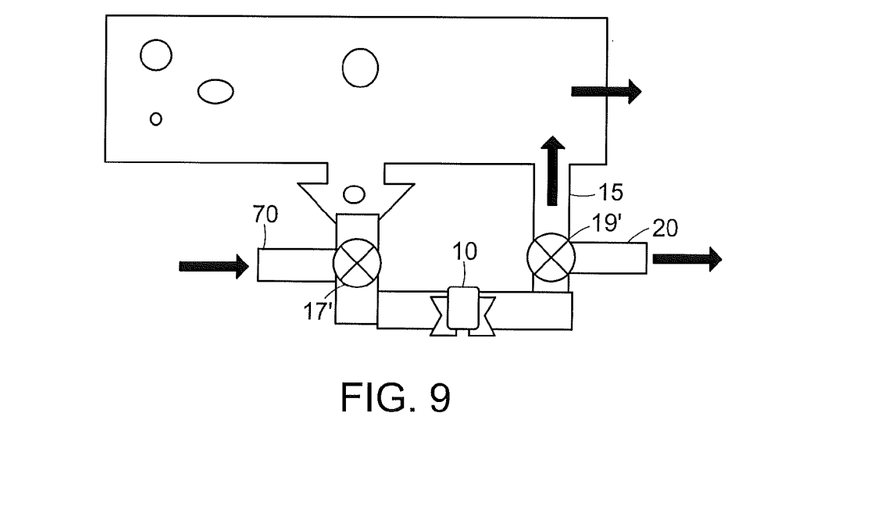
FIG. 9 is a schematic illustrating another embodiment of on-line implementation of a flow-through sensor on a pipe in accord with the present invention.

An alternative embodiment for implementation of a device 10 of the present invention in a by-pass conduit is illustrated in FIG. 9. In this embodiment the valves 17', 19' in the by-pass conduit are three-way valves and another conduit 70 is connected to the valves. This configuration permits a calibration fluid to be flowed into the sensor for calibration of the sensor. It also allows the sensor to be flushed periodically, as desired.

Preferably, a temperature probe or other temperature measuring device (not shown) is provided in the sensor chamber, or temperature readings are provided by other means from the medium being measured, so that changes in medium temperature can be monitored and appropriate corrections can be made, if desired, to sound wave property measurements to obtain more accurate attenuation or sound speed spectrum.

Figure 10A:
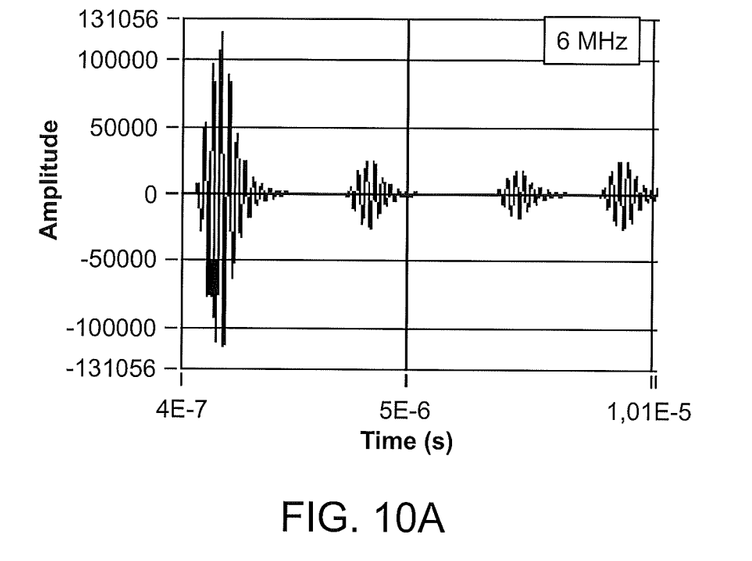
FIGS. 10(a) and 10(b) are examples of echo waveforms from a sensor having a transducer with a quartz delay rod and a reflector having two mirrored surfaces in a stepped arrangement such as illustrated in FIG. 5.
Figure 10B:
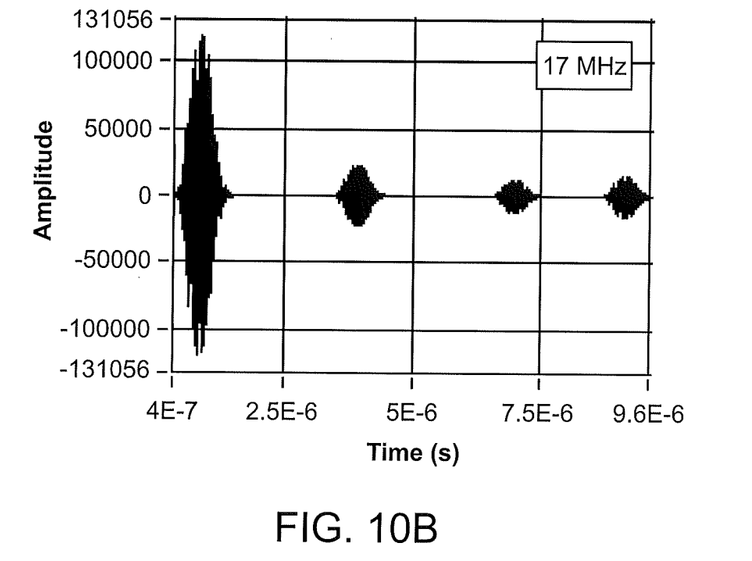

FIGS. 10(a) and 10(b) show examples of waveform captures for echoes from a sensor in water at 22° C., where the sensor used a 1" (2.54 cm) diameter, 5.6 cm long quartz delay rod and a stepped reflector having two surfaces, one being 0.4 cm further from the transducer, at frequencies of 6 and 17 MHz, respectively. From left to right in each figure, the waveforms are identified as follows:

First waveform: Reference echo traveling within the Quartz buffer (delay) rod.

Second waveform: First echo from the first (closer) reflector surface.

Third waveform: Second echo from the first (closer) reflector surface.

Fourth waveform: First echo from the second (farther) reflector surface.

Attenuation is calculated as follows: Attenuation=$20*\log(I_o/I_f)$, where $I_o$ is the reference echo amplitude, and $I_f$ is the fluid echo amplitude.

Attenuation frequency data obtained by the sensor analysis is input to inversion software, such as that provided by Lucent Technologies as is well known to those skilled in the art. The particle size distribution of particles in the fluid in the on-line sensor device thus can be obtained and used for process control in real time.

In use, a sensor in accord with this invention can be positioned in a by-pass conduit which is attached to a pipe or vessel of an industrial process. The sensor is calibrated with water, or preferably with the process fluid to be monitored and appropriate corrections are input to the inversion software using procedures well known to those skilled in the art. The two valves on either side of the sensor in the by-pass conduit are opened to permit either process medium or calibration/cleaning fluid to flow into and through the sensor. Attenuation measurements are made at the desired frequencies to obtain an attenuation spectrum. The attenuation spectrum can be used to control a process parameter in real time to control particle size characteristics of the particles in the process medium. The valves can be closed, if desired, to make static attenuation measurements or to make real time measurements periodically.

The invention has been described in detail including preferred embodiments thereof. However, it will be appreciated that those skilled in the art may make modifications and improvements within the spirit and scope of this invention.

What is claimed is:

1. A flow-through device for use on-line in a conduit capable of determining real-time characteristics of particles dispersed in a medium, the device comprising a sensor conduit, wherein the sensor comprises:
   a first stationary transducer positioned in a wall of the device to emit sound waves into the medium; and
   a fixed reflector or a second stationary transducer positioned opposite the first stationary transducer,
   wherein the sensor provides a plurality of different acoustic path lengths through the medium between the transducer and reflector or between the two transducers, thereby providing a plurality of different acoustic path lengths in the sensor without moving the transducers or reflector,
   wherein the first transducer is both an emitter and a receiver,
   wherein the first transducer includes a delay, and
   wherein the delay is implemented using a quartz rod having an end with a stepped configuration with a plurality of surfaces opposite and facing a single mirror reflector surface to provide a plurality of different echo path lengths.

2. The device of claim 1, wherein the quartz rod has grooves on its surface.

3. The device of claim 1, wherein the reflector comprises a stepped configuration having a plurality of mirrored surfaces opposite the transducer providing different echo path lengths.

4. The device of claim 1, wherein the reflector comprises a plurality of separate mirror surfaces, each mirror surface providing a different echo path length.

5. A flow-through device for use on-line in a conduit capable of determining real-time characteristics of particles dispersed in a medium, the device comprising a sensor conduit, wherein the sensor comprises:
   a first stationary transducer positioned in a wall of the device to emit sound waves into the medium; and
   a fixed reflector or a second stationary transducer positioned opposite the first stationary transducer,
   wherein the sensor provides a plurality of different acoustic path lengths through the medium between the transducer and reflector or between the two transducers, thereby providing a plurality of different acoustic path lengths in the sensor without moving the transducers or reflector, and
   wherein the sensor comprises a pair of stationary transducers at least one of which is assembled with a delay having an end with a stepped configuration with a plurality of surfaces opposite and facing the other transducer.

6. The device of claim 5, wherein the delay is implemented using a quartz rod.

7. A method for determining the characteristics of particles dispersed in a medium in real time for an industrial process, the method comprising:
   providing a flow-through device for use on-line in a conduit capable of determining real-time characteristics of particles dispersed in a process medium, the device comprising a sensor, wherein the sensor comprises:
     a first stationary transducer positioned in a wall of the device to emit sound waves into the medium; and
     a second stationary transducer positioned opposite the first stationary transducer,
     wherein the sensor provides a plurality of different acoustic attenuation path lengths through the medium between the two transducers, thereby providing a plurality of different path lengths in the sensor and no moving parts for the transducers, and
     wherein the first and second stationary transducers are provided such that at least one of the first and second stationary transducers is assembled with a delay having an end with a stepped configuration with a plurality of surfaces opposite and facing the other transducer;
   permitting a sample having particles dispersed in a medium to flow from the conduit into the sensor for determining the characteristics of the particles; and
   using the sensor to obtain attenuation and/or sound speed of sound waves for particular frequencies to provide an attenuation and/or sound speed spectrum.

8. A method of controlling particle size distribution in real time in a process, said method comprising:
   providing a flow-through device for use on-line in a conduit and capable of determining real-time characteristics of particles dispersed in a process medium, the device comprising a sensor, wherein the sensor comprises:
     a first stationary transducer positioned in a wall of the device to emit sound waves into the medium; and
     a second stationary transducer positioned opposite the first stationary transducer,
     wherein the sensor provides a plurality of different acoustic attenuation path lengths through the medium between the two transducers, thereby providing a plurality of different path lengths in the sensor with no moving parts for the transducers, and
     wherein the first and second stationary transducers are provided such that at least one of the first and second stationary transducers is assembled with a delay having an end with a stepped configuration with a plurality of surfaces opposite and facing the other transducer;
   permitting a sample having particles dispersed in a medium to flow from the conduit into the sensor for determining the characteristics of the particles;
   using the sensor to obtain attenuation and/or sound speed of sound waves for particular frequencies to provide an attenuation and/or sound speed spectrum; and
   using the obtained spectrum to control a process parameter to maintain desired characteristics of the particles in the process medium.

* * * * *